US010688867B2

(12) United States Patent
Wilson et al.

(10) Patent No.: US 10,688,867 B2
(45) Date of Patent: Jun. 23, 2020

(54) VEHICULAR MEDICAL ASSISTANT

(71) Applicant: International Business Machines Corporation, Armonk, NY (US)

(72) Inventors: John D. Wilson, League City, TX (US); Kelley Anders, East New Market, MD (US); David B. Lection, Raleigh, NC (US); Jeremy R. Fox, Georgetown, TX (US); Mark B. Stevens, Austin, TX (US); Liam S. Harpur, Dublin (IE); Jonathan Dunne, Dungarvan (IE); Maharaj Mukherjee, Poughkeepsie, NY (US); Jonathan Lenchner, Nairobi (KE)

(73) Assignee: International Business Machines Corporation, Armonk, NY (US)

( * ) Notice: Subject to any disclaimer, the term of this patent is extended or adjusted under 35 U.S.C. 154(b) by 94 days.

(21) Appl. No.: 15/985,802

(22) Filed: May 22, 2018

(65) Prior Publication Data

US 2019/0359056 A1    Nov. 28, 2019

(51) Int. Cl.
*B60K 28/06* (2006.01)
*G08B 21/06* (2006.01)
(Continued)

(52) U.S. Cl.
CPC ............ *B60K 28/06* (2013.01); *A61B 5/6893* (2013.01); *G08B 21/06* (2013.01); *A61B 5/0002* (2013.01);
(Continued)

(58) Field of Classification Search
CPC ......... B60K 28/06; A61B 5/6893; A61B 5/18; A61B 5/0002; G08B 21/06; B60N 2/002;
(Continued)

(56) References Cited

U.S. PATENT DOCUMENTS 6,927,694 B1    8/2005  Smith
7,254,439 B2    8/2007  Misczynski
(Continued)

FOREIGN PATENT DOCUMENTS

CN        102227612 A     10/2011
DE    112012004767 T5     11/2014
(Continued)

OTHER PUBLICATIONS

List of IBM Patents or Patent Applications Treated as Related. Filed May 22, 2018. 2 pages.
(Continued)

*Primary Examiner* — Russell Frejd
(74) *Attorney, Agent, or Firm* — Stosch Sabo

(57) ABSTRACT

A vehicular medical assistant configured to access a medical data store of interrelated diagnostic data, medical conditions, and mitigation actions. The vehicular medical assistant detects a medical event based on the medical data store and a set of data associated with the passenger. The set of data associated with the passenger can include biometric data, aural data, visual data, and environmental data. The vehicular medical assistant can implement a mitigation action in response to detecting the medical event. The mitigation action can include interacting with the passenger and/or modifying the vehicle.

18 Claims, 12 Drawing Sheets

(51) Int. Cl.
  *A61B 5/00* (2006.01)
  *B60N 2/00* (2006.01)
  *A61B 5/18* (2006.01)
  *B60W 50/00* (2006.01)
  *G05D 1/00* (2006.01)
(52) U.S. Cl.
  CPC .............. *A61B 5/18* (2013.01); *B60N 2/002* (2013.01); *B60W 2050/0062* (2013.01); *B60W 2540/26* (2013.01); *G05D 1/0055* (2013.01)
(58) Field of Classification Search
  CPC ...... B60W 2050/0062; B60W 2540/26; G05D 1/0055
  See application file for complete search history.

(56) References Cited

U.S. PATENT DOCUMENTS

| | | | |
|---|---|---|---|
| 7,427,924 B2 | 9/2008 | Ferrone | |
| 7,979,173 B2 | 7/2011 | Breed | |
| 8,725,311 B1 | 5/2014 | Breed | |
| 9,599,986 B1 | 3/2017 | Eberbach | |
| 2006/0200008 A1 | 9/2006 | Moore-Ede | |
| 2010/0100510 A1 | 4/2010 | Balaban | |
| 2012/0112879 A1* | 5/2012 | Ekchian | A61B 5/117 340/5.53 |
| 2013/0166323 A1* | 6/2013 | Heath | G06Q 50/22 705/3 |
| 2014/0135598 A1 | 5/2014 | Weidl | |
| 2014/0309806 A1 | 10/2014 | Ricci | |
| 2015/0081209 A1* | 3/2015 | Yeh | G06F 16/60 701/427 |
| 2015/0149023 A1 | 5/2015 | Attard | |
| 2016/0135706 A1* | 5/2016 | Sullivan | A61B 5/0059 600/301 |
| 2016/0167672 A1* | 6/2016 | Krueger | H04N 13/366 340/576 |
| 2016/0303969 A1 | 10/2016 | Akula | |
| 2017/0057492 A1* | 3/2017 | Edgington | B60K 28/066 |
| 2017/0071531 A1* | 3/2017 | Ehrhart | A61B 5/486 |
| 2017/0105104 A1 | 4/2017 | Ulmansky | |
| 2017/0108342 A1 | 4/2017 | Foreman | |
| 2017/0108862 A1* | 4/2017 | Mikkelsen | B60W 30/09 |
| 2017/0151959 A1 | 6/2017 | Boesen | |
| 2017/0247000 A1* | 8/2017 | Ricci | G06K 9/00302 |

FOREIGN PATENT DOCUMENTS

| | | |
|---|---|---|
| JP | 2015133050 A | 7/2015 |
| WO | 2017018842 A1 | 2/2017 |
| WO | 2017018852 A1 | 2/2017 |

OTHER PUBLICATIONS

Wilson, et al., "System and Method for Rendezvous Coordination of an Autonomous Automotive Vehicle With an Ambulance", U.S. Appl. No. 15/986,116, filed May 22, 2018.

Wilson, et al., "Autonomous Vehicle Coordination With Medical Facility", U.S. Appl. No. 15/985,863, filed May 22, 2018.

Burchell, Bill; Etihad Introduces Onboard Passenger Health Monitoring; Feb. 25, 2010; http://aviationweek.com/awin/etihad-introduces-onboard-passenger-health-monitoring; 2 pages.

D'Allegro, Joe; Soon your car will know when you are having a heart attack- and know how to react; CNBC.com; Nov. 17, 2017; https://www.cnbc.com/2017/11/17/cars-will-know-when-youre-having-a-heart-attack-and-how-to-react.html; 6 pages.

De Lille, Christing; Flightbeat; https://www.tudelft.nl/en/ide/research/research-labs/aviation/education/flightbeat/; retrieved from the Internet Nov. 6, 2018; 3 pages.

Kavitha, K.C. et al.; Smart wireless healthcare monitoring for drivers community; 2014 International Conference on Communication and Signal Processing; Apr. 3-5, 2014; 2 pages.

Patil, Savita; In-Vehicle Driver Health Monitoring System; International Journal of Technology and Science, ISSN (Online 2350-1111, (Print) 2350-1103; vol. 9, Issue 2; 2016; pp. 38-40.

Prigg, Mark; Engineers develop a car that can monitor your HEALTH as you drive—and take over if you become ill or fall asleep; Jul. 11, 2013; http://www.dailymail.co.uk/sciencetech/article-2360694/Ford-car-monitor-HEALTH-drive--ill-fall-asleep.html; 4 pages.

Safe Car News; Ford combines driver health monitoring and ADAS; Jan. 12, 2016; http://safecarnews.com/ford-combines-driver-health-monitoring-and-adas_ja7126/; 6 pages.

Strickland, Eliza; 3 Ways Ford Cars Could Monitor Your Health; IEEE Spectrum; May 19, 2017; https://spectrum.ieee.org/the-human-os/biomedical/diagnostics/3-ways-ford-cars-could-monitor-your-health; 7 pages.

Tata Elxsi; In-car health and wellness monitoring; http://www.tataelxsi.com/Perspectives/WhitePapers/In%20car%20wellness.pdf; retrieved from the Internet Nov. 6, 2018; 10 pages.

Wilson et al., "Autonomous Vehicle Monitoring", U.S. Appl. No. 16/182,012, filed Nov. 6, 2018.

IBM, List of IBM Patents or Patent Applications Treated as Related, Nov. 7, 2018, 2 pages.

"Autonomous Vehicle Biometric Medical Emergency Index", An IP.com Prior Art Database Technical Disclosure, Disclosed Anonymously, IP.com No. IPCOM000252775D, IP.com Electronic Publication Date: Feb. 8, 2018, 4 pages, Evidence of Grace Period Use or Sale.

"OnStar", Wikipedia, this page was last edited on Feb. 28, 2018, 7 pages, <https://en.wikipedia.org/wiki/OnStar>.

"Seizure While Driving", Epilepsy Foundation, last printed Mar. 13, 2018, 25 pages, <https://www.epilepsy.com/connect/forums/living-epilepsy-adults/seizure-while-driving-1>.

Mell et al., "The NIST Definition of Cloud Computing", National Institute of Standards and Technology, Special Publication 800-145, Sep. 2011, 7 pages.

Van Wagenen, Juliet, "The Next Generation of Ambulance Technology Hits the Road", HealthTech, Copyright © 2018 CDW LLC, 5 pages, <https://healthtechmagazine.net/article/2017/04/next-generation-ambulance-technology-hits-road>.

\* cited by examiner

500 — 502, 504, 506, 508, 510, 512

| SENSOR | DATA | NORMAL | CONCERNED | EMERGENCY | SCORE |
|---|---|---|---|---|---|
| 1 | 98 | 97-99 | 95<X<97 OR 99<X<102 | X ≤ 95 OR X ≥ 102 | W1*F1(X1) |
| 2 | 18 | 10-25 | 3<X<10 OR X>45 | X ≤ 3 | W2*F2(X2) |
| 3 | NORMAL | NORMAL | GESTICULATIONS_1 | GESTICULATIONS_2 | W3*F3(X3) |
| 4 | "HELLO" | NORMAL | DICT1_HEALTH_CONDITIONS | DICT2_HEALTH_EMERGENCY | W4*F4(X4) |
| ... | ... | ... | ... | ... | W..*F..(X..) |
| N | X | ... | ... | ... | WN*FN(XN) |

| MEDICAL CONDITION | SENSOR DATA |
|---|---|
| UNCONSCIOUS | RULE_1 |
| FEVER | RULE_2 |
| NAUSEOUS | RULE_3 AND RULE_4 |
| CHOKING | RULE_5 OR RULE_6 |
| HEART ATTACK | RULE_7 |
| ... | ... |

| ACTIONS | CONDITIONS |
|---|---|
| USE SPEAKERS TO WAKE PASSENGER | MEDICAL_CONDITIONS_X OR SCORES_N |
| REROUTE VEHICLE | ... |
| TURN ON VEHICLE EMERGENCY SIRENS/LIGHTS | ... |
| REQUEST HELP OVER EXTERNAL SPEAKER | ... |
| NOTIFY EMERGENCY AUTHORITY | ... |
| INCREASE VEHICLE TEMPERATURE | ... |
| DECREASE VEHICLE TEMPERATURE | ... |
| DISPENSE MEDICAL AID | ... |
| ... | ... |

FIG. 5C

VEHICULAR MEDICAL ASSISTANT

STATEMENT REGARDING PRIOR DISCLOSURES BY THE INVENTOR OR A JOINT INVENTOR

A document titled "Autonomous Vehicle Biometric Medical Emergency Index", published on the website https://priorart.ip.com/IPCOM/000252775 on Feb. 8, 2018, made by one or more inventors listed in the current application, and submitted in an Information Disclosure Statement herewith, is hereby considered a Grace Period Disclosure and recognized as an exception to 35 U.S.C. § 102(a)(1) prior art.

BACKGROUND

The present disclosure relates to emergency management and, more specifically, to mitigating a medical event of a passenger in a vehicle.

SUMMARY

Aspects of the present disclosure are directed toward a computer-implemented for mitigating a medical event in a vehicle. The method can comprise accessing a medical data store comprising diagnostic data, medical conditions, and mitigation actions. The diagnostic data, medical conditions, and mitigation actions can be interrelated using machine learning algorithms. The method can further comprise detecting a medical event based on a set of data associated with a passenger in the vehicle and the medical data store. The set of data associated with the passenger can be received from a plurality of sensors in the vehicle. The plurality of sensors can comprise a biometric sensor collecting biometric data from the passenger, an aural sensor collecting aural data from the passenger, a visual sensor collecting visual data from the passenger, and an environmental sensor collecting environmental data from the vehicle. The set of data associated with the passenger can comprise the aural data, the biometric data, the visual data, and the environmental data. The method can further comprise implementing a mitigation action in response to detecting the medical event. The mitigation action can comprise an interaction with the passenger and a modification to the vehicle.

Further aspects of the present disclosure are directed toward a system for mitigating a medical event in a vehicle. The system can comprise a processor and a computer-readable storage medium storing instructions, which, when executed by the processor, are configured to cause the processor to perform a method comprising accessing a medical data store comprising diagnostic data, medical conditions, and mitigation actions. The diagnostic data, medical conditions, and mitigation actions can be interrelated using machine learning algorithms. The method can further comprise detecting a medical event based on a set of data associated with a passenger in the vehicle and the medical data store. The set of data associated with the passenger can be received from a plurality of sensors in the vehicle. The plurality of sensors can comprise a biometric sensor collecting biometric data from the passenger, an aural sensor collecting aural data from the passenger, a visual sensor collecting visual data from the passenger, and an environmental sensor collecting environmental data from the vehicle. The set of data associated with the passenger can comprise the aural data, the biometric data, the visual data, and the environmental data. The method can further comprise implementing a mitigation action in response to detecting the medical event. The mitigation action can comprise an interaction with the passenger and a modification to the vehicle.

Further aspects of the present disclosure are directed toward a computer program product for mitigating a medical event in a vehicle. The computer program product can comprise a computer readable storage medium having program instructions executable by a processor to cause the processor to perform a method comprising accessing a medical data store comprising diagnostic data, medical conditions, and mitigation actions. The diagnostic data, medical conditions, and mitigation actions can be interrelated using machine learning algorithms. The method can further comprise detecting a medical event based on a set of data associated with a passenger in the vehicle and the medical data store. The set of data associated with the passenger can be received from a plurality of sensors in the vehicle. The plurality of sensors can comprise a biometric sensor collecting biometric data from the passenger, an aural sensor collecting aural data from the passenger, a visual sensor collecting visual data from the passenger, and an environmental sensor collecting environmental data from the vehicle. The set of data associated with the passenger can comprise the aural data, the biometric data, the visual data, and the environmental data. The method can further comprise implementing a mitigation action in response to detecting the medical event. The mitigation action can comprise an interaction with the passenger and a modification to the vehicle.

The above summary is not intended to describe each illustrated embodiment or every implementation of the present disclosure.

BRIEF DESCRIPTION OF THE DRAWINGS

The drawings included in the present application are incorporated into, and form part of, the specification. They illustrate embodiments of the present disclosure and, along with the description, serve to explain the principles of the disclosure. The drawings are only illustrative of certain embodiments and do not limit the disclosure.

FIG. 5A illustrates an example medical risk assessment value table in accordance with some embodiments of the present disclosure.

FIG. 5B illustrates an example medical condition table in accordance with some embodiments of the present disclosure.

FIG. 5C illustrates an example mitigation action table in accordance with some embodiments of the present disclosure.

Figure 1:
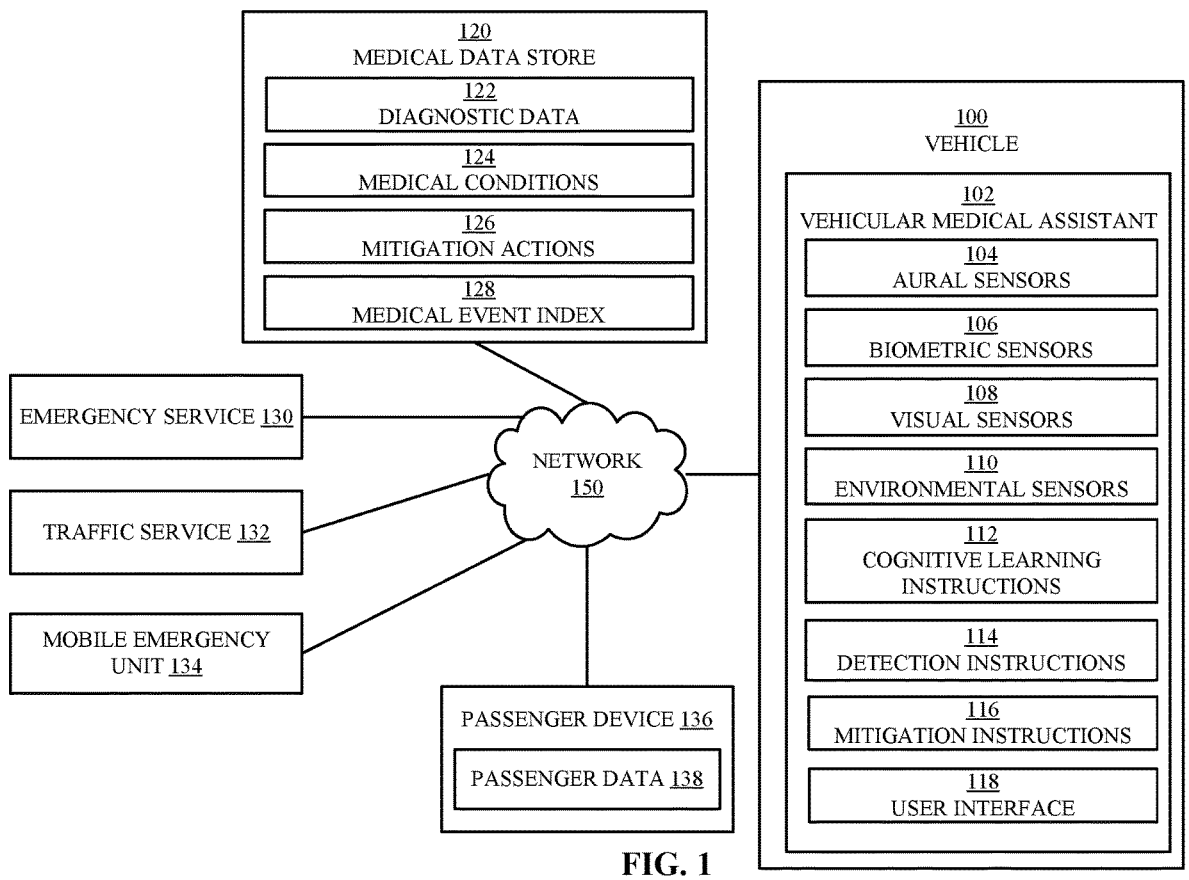
FIG. 1 illustrates a block diagram of an example Internet of Things (IoT) environment in accordance with some embodiments of the present disclosure.

While the present disclosure is amenable to various modifications and alternative forms, specifics thereof have been shown by way of example in the drawings and will be described in detail. It should be understood, however, that the intention is not to limit the present disclosure to the particular embodiments described. On the contrary, the intention is to cover all modifications, equivalents, and alternatives falling within the spirit and scope of the present disclosure.

DETAILED DESCRIPTION

Aspects of the present disclosure are directed toward automated medical assistance and, more specifically, to providing automated medical assistance to passengers in autonomous, semi-autonomous, and/or non-autonomous vehicles. While the present disclosure is not necessarily limited to such applications, various aspects of the present disclosure may be appreciated through a discussion of various examples using this context.

In accordance with some embodiments of the present disclosure, medical assistance can be provided in a vehicle based on information derived from a network of sensors in an Internet of Things (IoT) configuration. In embodiments of the present disclosure, the IoT can be a network of physical devices having electronics, hardware, software, sensors, actuators, and/or network connectivity and configured to generate data, share data, and implement actions based on the shared data. The physical devices can include, but are not limited to, cameras (e.g., visual/audio cameras, thermal cameras, etc.), microphones, heart rate monitors, blood pressure monitors, wearable devices, pedometers, directional thermometers, odor sensors, moisture sensors, air composition sensors, accelerometers, medical devices, diagnostic devices, and so on. The physical devices can further include vehicular devices such as, but not limited to, navigation equipment, environmental controls, and communication equipment. The physical devices can further include other physical devices such as, but not limited to, traffic sensors (e.g., traffic lights, congestion sensors, traffic cameras, etc.), mobile emergency unit sensors (e.g., locations of ambulances), and so on.

Aspects of the present disclosure monitor one or more passengers in a vehicle using a vehicular medical assistant. The vehicular medical assistant can monitor passenger health using one or more sensors. The vehicular medical assistant can use cognitive computing (also referred to as machine learning algorithms herein) to identify a medical event (e.g., choking, heart attack, nausea, etc.) based on the data collected from the one or more sensors and compared with information in a medical data store. The vehicular medical assistant can execute one or more actions and/or one or more interactions in response to detecting a medical event. Actions can include, but are not limited to, rerouting the vehicle, stopping the vehicle, notifying an emergency authority, and so on. Interactions can include, but are not limited to, providing instructions to the passenger, attempting to wake an unconscious passenger, providing a medical aid to the passenger (e.g., a bandage, an antiseptic, a disinfectant, a medication, a vomit bag, an epinephrine autoinjector, an opiate antidote, an inhaler, etc.), communicating with the passenger, and so on.

Aspects of the present disclosure realize numerous advantages such as, but not limited to, increased vehicular safety. For example, in non-autonomous vehicles, aspects of the present disclosure can determine a driver is falling asleep and wake the driver, communicate with an emergency authority during a medical event, and/or provide medical instruction to one or more passengers. In semi-autonomous vehicles, in addition to the safety advantages discussed above for non-autonomous vehicles, aspects of the present disclosure can safely stop a car if a driver is temporarily disabled (e.g., if a driver has a seizure while driving, a semi-autonomous vehicle can temporarily control the vehicle to stop the vehicle on the side of the road). In autonomous vehicles, in addition to the safety advantages discussed above for non-autonomous vehicles and semi-autonomous vehicles, an autonomous vehicle can reroute the vehicle to an emergency center (e.g., hospital, urgent care center, fire station, police station, etc.) during a medical emergency. Thus, aspects of the present disclosure improve passenger/driver safety in non-autonomous, semi-autonomous, and/or autonomous vehicles.

As a second example advantage, aspects of the present disclosure employ cognitive learning to increase the accuracy of detected medical events and increase the effectiveness of mitigation actions executed in response to detecting a medical event. Cognitive learning is uniquely suited to the field of medical event detection and mitigation due to the complicated relationships between medical measurements, symptoms, conditions, risks, and mitigation techniques. As one example illustrating the advantages of cognitive learning over predefined, static rules, a blood pressure reading of 145/96 may be a highly elevated and abnormal reading for a first person, while a blood pressure reading of 145/96 may be consistent with a second person's average blood pressure reading. Thus, the blood pressure measurement for the first individual may indicate an acute medical emergency, while the same blood pressure measurement associated with the second individual may indicate a chronic health condition rather than an acute medical emergency. To differentiate the acute medical emergency from the chronic health condition, aspects of the present disclosure can account for other factors such as, but not limited to, heart rate, temperature, pupil dilation, perspiration, gesticulation analysis, aural indications (e.g., groaning, retching), natural language processing (e.g., a response to a question "are you feeling ok?"), and so on. Thus, cognitive learning advantageously improves a vehicular medical assistant based on the capability of cognitive computing to identify multivariate indicators, factors, and/or correlations between large amounts of aural data, biometric data, visual data, and/or environmental data, thereby improving accuracy of identified medical events and improving passenger health outcomes associated with implemented mitigation actions.

Thus, aspects of the present disclosure exhibit numerous advantages. However, not all advantages are listed, and aspects of the present disclosure exist that can contain, all, some, or none of the aforementioned advantages while remaining within the spirit and scope of the present disclosure.

Referring now to FIG. 1, illustrated is a block diagram of an example IoT environment according to aspects of the present disclosure. The IoT environment can include numerous components communicatively coupled by a network 150 such as, but not limited to, a vehicular medical assistant 102 located in a vehicle 100, a medical data store 120, an emergency service 130, a traffic service 132, a mobile emergency unit 134, and a passenger device 136.

Vehicle 100 can comprise a non-autonomous vehicle, a semi-autonomous vehicle, or an autonomous vehicle according to various embodiments. Vehicle 100 can be a sedan, sport-utility-vehicle (SUV), truck, bus, all-terrain vehicle (ATV), aerial vehicle (e.g., plane, helicopter, etc.), train, ship (e.g., ferry, cruise liner, etc.), or a different form of vehicular transport.

Vehicle 100 can include a vehicular medical assistant 102 configured to detect and mitigate medical events experienced by a passenger in vehicle 100. Although vehicular medical assistant 102 is shown within vehicle 100, vehicular medical assistant 102 can likewise be communicatively coupled to, but physically removed from, vehicle 100. For example, in some embodiments, aspects of vehicular medical assistant 102 can be provided as a service to vehicle 100 and utilize existing technology within vehicle 100 such as a display interface, autonomous or semi-autonomous driving technology, speakers, and other aspects of vehicle 100 to virtually provide aspects of vehicular medical assistant 102. In some embodiments, vehicular medical assistant 102 comprises a discrete unit physically integrated into vehicle 100 (e.g., integrated into the vehicle during assembly, or attached as an after-market accessory).

Vehicular medical assistant 102 can include aural sensors 104 collecting aural data from a passenger in the vehicle 100, biometric sensors 106 collecting biometric data from the passenger in the vehicle 100, visual sensors 108 collecting visual data from the passenger in the vehicle 100, and environmental sensors 110 collecting environmental data from the vehicle 100. Vehicular medical assistant 102 can further include cognitive learning instructions 112 configured to learn (e.g., identify, quantify, and/or model) interrelationships between diagnostic data, medical conditions, and mitigation actions. Vehicular medical assistant 102 can further include detection instructions 114 configured to detect a medical event and mitigation instructions 116 configured to mitigate a medical event. Vehicular medical assistant 102 can further include a user interface 118 for verbally, textually, and/or visually interacting with a passenger in vehicle 100.

Aural sensors 104 can be sensors configured to detect sounds such as speech, choking sounds, retching sounds, coughing sounds, breathing levels (e.g., hyperventilation), groans, and so on. In some embodiments, aural sensors 104 can be calibrated to detect sounds from an area defined by a direction and a range. In some embodiments, aural sensors 104 can be calibrated to detect sounds within a certain frequency range (e.g., 20-20,000 hertz) and/or within a certain volume (e.g., 0-130 decibels).

Biometric sensors 106 can include active sensors and passive sensors. Active sensors are sensors requiring user interaction to derive medical information from the user. Active sensors can include, but are not limited to, some blood pressure monitors (e.g., measured by a pressurized cuff on a passenger's arm), some heart rate monitors (e.g., contacting a passenger on the chest, wrist, palm, finger, or a different location), and some blood sugar level monitors (e.g., requiring blood sampling using a lancet). Passive sensors are sensors collecting medical information from a user without requiring user engagement and/or action. Passive sensors can include, but are not limited to, thermometers (e.g., directional thermometers, thermal video cameras, etc.), odor sensors (e.g., chemosensors, sensors utilizing gas chromatography, etc.), and other sensors.

Visual sensors 108 can include video cameras capable of capturing passenger behaviors (e.g., movements, gesticulations), color variation (e.g., pale, flushed, etc.), perspiration (e.g., changes in facial reflectivity), pupil dilation, blinking (e.g., blinks per minute, eyes closed, etc.), breathing (e.g., breaths per minute, intensity of breathing, etc.), and other conscious and unconscious behaviors which may be indicative of a passenger's health.

Environmental sensors 110 can include sensors measuring temperature, humidity, oxygen content, acceleration, and/or other features of the passenger area. Environmental sensors 110 can include, but are not limited to, a thermometer, a humidity sensor, an accelerometer (e.g., measuring passenger position in a seat), an air composition sensor, and other sensors.

Cognitive learning instructions 112 can include processor-executable instructions for ingesting a medical data store 120 and generating correlations, associations, interrelations, predictions, expectations, confidence-levels, thresholds, algorithms, models, and/or other insights related to detecting and mitigating a medical event. In some embodiments, cognitive learning instructions 112 are configured to generate medical event index 128.

Detection instructions 114 can include processor-executable instructions for detecting a medical event based on the data collected from aural sensors 104, biometric sensors 106, visual sensors 108, and/or environmental sensors 110. Detection instructions 114 can include instructions for matching a set of collected data to a known combination of data indicating a medical event. In some embodiments, detection instructions 114 rank, score, or otherwise approximate an urgency associated with the detected medical event.

Mitigation instructions 116 can include processor-executable instructions for mitigating the medical event. Mitigation instructions 116 can include instructions for interacting with the passenger via a user interface 118, rerouting the vehicle carrying the passenger, altering the environmental conditions of the vehicle carrying the passenger, notifying an emergency authority, and/or other mitigation actions.

User interface 118 can be a user interface capable of presenting questions to a passenger (e.g., verbally and/or visually) and collecting feedback from the user (e.g., verbal feedback, movement-based feedback, and/or tactile feedback).

Vehicular medical assistant 102 can be connected to medical data store 120 via network 150. Medical data store 120 can store structured, semi-structured, and/or unstructured medical data relevant to detecting and mitigating a medical event in the vehicle 100. Medical data store 120 can include diagnostic data 122, medical conditions 124, mitigation actions 126, and medical event index 128. Diagnostic data 122 can comprise numeric and/or textual measurements indicating normal and abnormal health conditions. In some embodiments, diagnostic data 122 includes data similar in nature to the data collected by aural sensors 104, biometric sensors 106, visual sensors 108, and/or environmental sensors 110.

Medical conditions 124 can comprise various combinations of diagnostic data indicating various medical conditions. For example, the medical condition 124 "unconscious" could be associated with diagnostic data 122 of eyes closed, a slumped posture, and unresponsive to interaction as detected by visual sensors 108. As another example, the medical condition 124 "choking" could be associated with diagnostic data 122 of "hands at throat" as detected by visual sensors 108 and coughing as detected by aural sensors 104. As another example, the medical condition 124 "fever" could be associated with diagnostic data 122 of three consecutive thermometer measurements on a passenger's forehead above 100° Fahrenheit as measured by biometric sensors 106. As another example, the medical condition 124 "mirror cut on hand" could be associated with diagnostic data 122 collected from visual sensors 108 and biometric sensors 108.

Mitigation actions 126 can be executed at the vehicle using mitigation instructions 116. Mitigation actions 126 can include, but are not limited to, rerouting the vehicle, changing environmental conditions in the vehicle cabin, interacting with the passenger, dispensing a medical aid to the passenger, and/or contacting an emergency authority on behalf of the passenger.

Medical event index 128 can interrelate the diagnostic data 122, the medical conditions 124, and the mitigation actions 126. Thus, medical event index 128 can be used to determine an appropriate mitigation action 126 for given diagnostic measurements 122 and/or given medical conditions 124.

Vehicular medical assistant 102 can also be communicatively coupled to emergency service 130 via network 150. Emergency service 130 can be an emergency authority such as, but not limited to, dispatchers associated with a police department, fire department, emergency medical service (EMS) department, hospital, a clinic, a regional authority (e.g., city, county, region), or a different dispatch service. Emergency service 130 can receive information from, and provide information to, the vehicular medical assistant 102.

Vehicular medical assistant 102 can also be communicatively coupled to traffic service 132 via network 150. Traffic service 132 can include traffic congestion information and/or traffic shaping functionality that may be used to plan routes, estimate arrival times, and/or change routes in real-time for the vehicle 100 in response to a medical event.

Vehicular medical assistant 102 can also be communicatively coupled to mobile emergency unit 134 via network 150. Mobile emergency unit 134 can be, but is not limited to, an ambulance, a fire truck, a police vehicle, or a different vehicle capable of resolving a medical event and/or facilitating transfer of a passenger to a hospital.

Vehicular medical assistant 102 can also be communicatively coupled to a passenger device 136. Passenger device 136 can comprise a wearable device, a health monitoring device, a mobile phone, a tablet, or a different device. Passenger device 136 can store passenger data 138. In some embodiments, passenger data 138 comprises historical health data of the passenger (e.g., average heart rate, health conditions, medications, risk factors, etc.).

Network 150 can comprise any physical or virtual network, including Wi Fi, broadband, cellular, short-range, and/or other networks. Although a single network is shown, multiple similar or dissimilar sub-networks may likewise be used to continuously or intermittently connect various components illustrated in FIG. 1.

FIG. 1 is intended to represent the major components of an example IoT environment according to embodiments of the present disclosure. In some embodiments, however, individual components can have greater or lesser complexity than shown in FIG. 1, and components other than, or in addition to those shown in FIG. 1 can be present. Furthermore, in some embodiments, various components illustrated in FIG. 1 can have greater, lesser, or different functionality than shown in FIG. 1. Further still, aspects of the present disclosure exist comprising only a subset of the components illustrated while remaining within the spirit and scope of the present disclosure. As one example, in some embodiments, only vehicular medical assistant 102 and medical event index 128 are used to implement aspects of the present disclosure.

Figure 2:
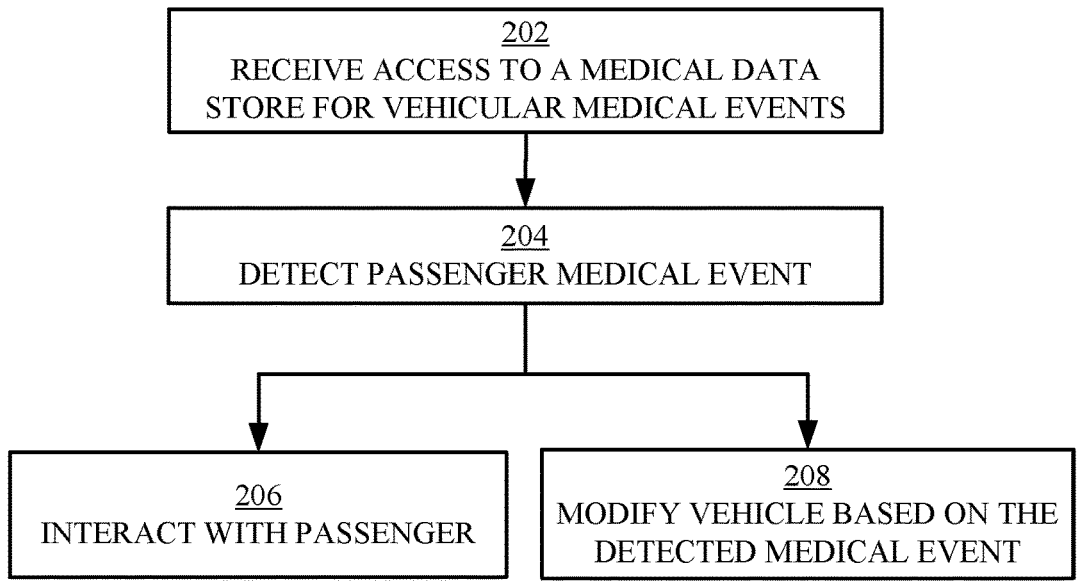
FIG. 2 illustrates a flowchart of an example method for managing a medical event in a vehicle in accordance with some embodiments of the present disclosure.

FIG. 2 illustrates a flowchart of an example method for managing a medical event in accordance with some embodiments of the present disclosure. In some embodiments, the method 200 is executed by a vehicular medical assistant (e.g., vehicular medical assistant 102 of FIG. 1 or vehicular medical assistant 1000 of FIG. 10), by a processor, or by a different set of hardware and software resources. For clarity, the method 200 will be described as being executed by a vehicular medical assistant, however, the method 200 can likewise be performed by alternative configurations of hardware.

In operation 202, the vehicular medical assistant can access a medical data store (e.g., medical data store 120 of FIG. 1). The medical data store can comprise diagnostic data, medical conditions, and mitigation actions useful for detecting and mitigating a medical event in a vehicle. The medical data store can further comprise interrelationships between diagnostic data, medical conditions, and mitigation actions. In some embodiments, the interrelationships are identified, quantified, and/or modeled using machine learning algorithms executed on the medical data store. The machine learning algorithms can generate additional information (e.g., definitions, algorithms, computations, insights, correlations, indications, analyses, or other interrelationships) useful for monitoring passenger health, detecting a medical event, and mitigating a detected medical event. Operation 202 is described in further detail hereinafter with respect to FIGS. 3, 4, and 5A-5C.

In operation 204, the vehicular medical assistant can detect a medical event. The medical event can be detected based on a set of data associated with a passenger in a vehicle and the medical data store accessed in operation 202. In some embodiments, the set of data associated with the passenger in the vehicle comprises aural data from the passenger and collected by one or more aural sensors (e.g., aural sensors 104 of FIG. 1), biometric data from the passenger and collected by one or more biometric sensors (e.g., biometric sensors 106 of FIG. 1), visual data from the passenger and collected by one or more visual sensors (e.g., visual sensors 108 of FIG. 1), and/or environmental data of the vehicle cabin and collected by one or more environmental sensors (e.g., environmental sensors 110 of FIG. 1). Operation 204 is described in further detail hereinafter with respect to FIGS. 6-7.

In operations 206 and 208, the vehicular medical assistant can implement a mitigation action in response to detecting the medical event. In some embodiments, the mitigation action comprises interacting with the passenger (e.g., operation 206) and/or modifying the vehicle (e.g., operation 208). As shown, operations 206 and 208 can occur approximately contemporaneously or sequentially according to various embodiments of the present disclosure. In some embodiments, aspects of operation 206 are related to aspects of operation 208 and vice versa. For example, in operation 208, the vehicular medical assistant can reroute the vehicle. In response to rerouting the vehicle, the vehicular medical assistant can notify the passenger that the vehicle is rerouted and indicate the new destination in operation 206.

In operation 206, the vehicular medical assistant can interact with the passenger in response to detecting the medical event. The vehicular medical assistant can interact with the passenger by communicating with the passenger (e.g., providing instructions to the passenger, asking the passenger health-related questions, providing a notification to the passenger, etc.) and/or providing medical aids to the passenger (e.g., a bandage, an antiseptic, a disinfectant, an epinephrine autoinjector, an opiate antidote, an inhaler, etc.). Operation 206 is described in more detail hereinafter with respect to FIG. 8.

In operation 208, the vehicular medical assistant can modify the vehicle based on the detected medical event. The vehicular medical assistant can modify the vehicle by, for example, altering the temperature of the vehicle, rerouting the vehicle to an emergency facility, notifying an emergency authority of the medical event, requesting assistance from bystanders regarding the medical event, and so on. Operation 208 is described in more detail hereinafter with respect to FIG. 9.

FIG. 2 is intended to represent the major operations of an example method for managing a medical event according to embodiments of the present disclosure. In some embodiments, however, individual operations can have greater or lesser complexity than shown in FIG. 2, and operations other than, or in addition to, those shown in FIG. 2 can be present. Furthermore, in some embodiments, various operations illustrated in FIG. 2 can have greater, lesser, or different functionality than shown in FIG. 2.

Figure 3:
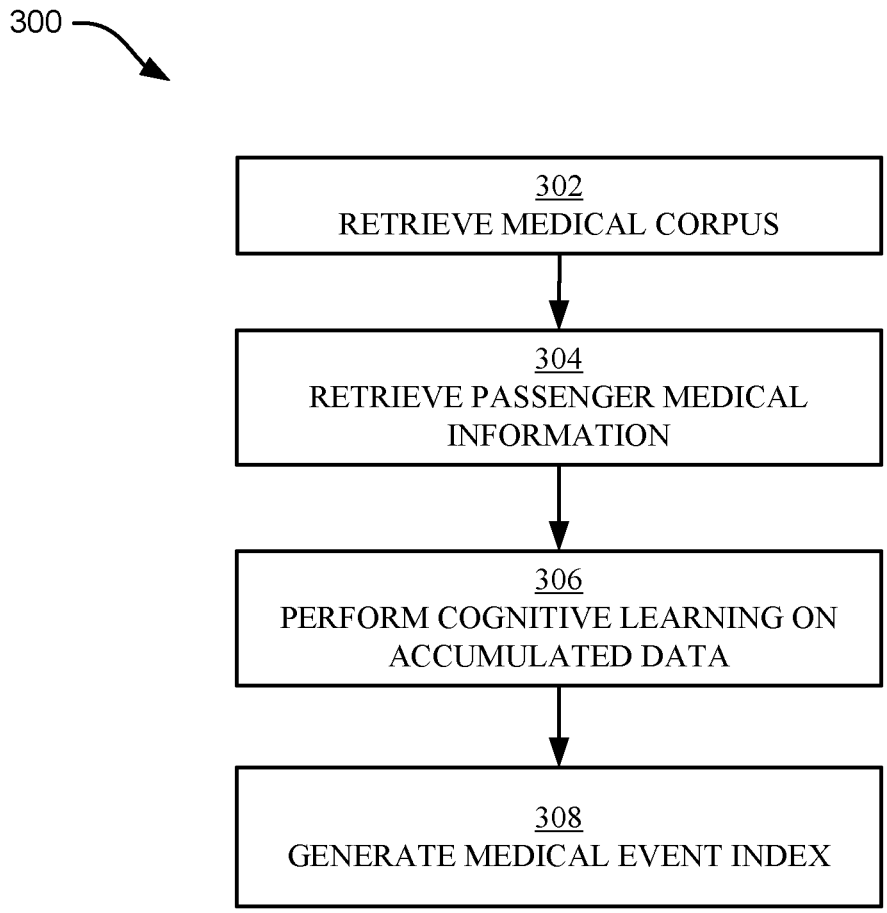
FIG. 3 illustrates a flowchart of an example method for generating a medical index in accordance with some embodiments of the present disclosure.

FIG. 3 illustrates a flowchart of an example method for generating a medical event index in accordance with some embodiments of the present disclosure. In some embodiments, the method 300 is executed by a vehicular medical assistant (e.g., vehicular medical assistant 102 of FIG. 1 or vehicular medical assistant 1000 of FIG. 10), by a processor, or by a different set of hardware and software resources. For clarity, the method 300 will be described as being executed by a vehicular medical assistant, however, the method 300 can likewise be performed by alternative configurations of hardware. In some embodiments, the method 300 is a sub-method of operation 202 of FIG. 2.

In operation 302, the vehicular medical assistant can retrieve a medical corpus. The medical corpus can comprise structured and unstructured data relevant to identifying and mitigating medical events in a vehicular environment. The medical corpus can comprise diagnostic data (e.g., diagnostic data 122 of FIG. 1), medical condition data (e.g., medical conditions 124 of FIG. 1), and/or mitigation data (e.g., mitigation actions 126 of FIG. 1).

In operation 304, the vehicular medical assistant retrieves passenger medical information. The vehicular medical assistant can collect passenger medical information such as, but not limited to, historical medical diagnostics (e.g., blood pressure readings, heart rate readings, diseases, conditions, symptoms, risk factors, etc.). In some embodiments, the vehicular medical assistant can retrieve passenger medical information from one or more passenger devices (e.g., passenger device 136 of FIG. 1). In some embodiments, the vehicular medical assistant can retrieve the medical information from a database storing the medical information of the passenger (e.g., an electronic health record).

For example, in some embodiments, the passenger could be a subscribing member to a ride-sharing service associated with the vehicle. The passenger could input his/her fingerprint into the system upon entering the vehicle. The fingerprint could be used to identify the passenger, generate invoicing, determine preferred routes, determine likely destinations, and store a history of the passenger's medical information. Thus, the vehicular medical assistant could retrieve passenger medical data based on a biometric identification of the passenger. Although a fingerprint was used in the previous example, alternative biometric identifiers are also possible. For example, eye characteristics, facial recognition, voice recognition, or a different factor or combination of factors could be used to identify a passenger.

In operation 306, the vehicular medical assistant can perform cognitive learning on the accumulated data (e.g., the data collected in operation 302 and/or the data collected in operation 304). The vehicular medical assistant can perform cognitive learning on the medical corpus and/or the passenger medical information to characterize normal and abnormal ranges of various health diagnostics, emergent health conditions, effective mitigation techniques for various emergent health conditions, and/or other interrelationships, correlations, indicators, predictors, confidence levels, and other insights relating diagnostic data, medical condition data, and mitigation actions.

Although not shown, the vehicular medical assistant can execute any number of machine learning algorithms such as, but not limited to, decision tree learning, association rule learning, artificial neural networks, deep learning, inductive logic programming, support vector machines, clustering, Bayesian networks, reinforcement learning, representation learning, similarity/metric training, sparse dictionary learning, genetic algorithms, rule-based learning, and/or other machine learning techniques.

For example, the vehicular medical assistant can be configured to perform machine learning using one or more of the following example techniques: K-nearest neighbor (KNN), learning vector quantization (LVQ), self-organizing map (SOM), logistic regression, ordinary least squares regression (OLSR), linear regression, stepwise regression, multivariate adaptive regression spline (MARS), ridge regression, least absolute shrinkage and selection operator (LASSO), elastic net, least-angle regression (LARS), probabilistic classifier, naïve Bayes classifier, binary classifier, linear classifier, hierarchical classifier, canonical correlation analysis (CCA), factor analysis, independent component analysis (ICA), linear discriminant analysis (LDA), multi-dimensional scaling (MDS), non-negative metric factorization (NMF), partial least squares regression (PLSR), principal component analysis (PCA), principal component regression (PCR), Sammon mapping, t-distributed stochastic neighbor embedding (t-SNE), bootstrap aggregating, ensemble averaging, gradient boosted decision tree (GBRT), gradient boosting machine (GBM), inductive bias algorithms, Q-learning, state-action-reward-state-action (SARSA), temporal difference (TD) learning, apriori algorithms, equivalence class transformation (ECLAT) algorithms, Gaussian process regression, gene expression programming, group method of data handling (GMDH), inductive logic programming, instance-based learning, logistic model trees, information fuzzy networks (IFN), hidden Markov models, Gaussian naïve Bayes, multinomial naïve Bayes, averaged one-dependence estimators (AODE), Bayesian network (BN), classification and regression tree (CART), chi-squared automatic interaction detection (CHAID), expectation-maximization algorithm, feedforward neural networks, logic learning machine, self-organizing map, single-linkage clustering, fuzzy clustering, hierarchical clustering, Boltzmann machines, convolutional neural networks, recurrent neural networks, hierarchical temporal memory (HTM), and/or other machine learning techniques.

In operation 308, the vehicular medical assistant can generate a medical event index based on the machine learning algorithms implemented in operation 306. The medical event index can interrelate various diagnostic data, medical conditions, and mitigation actions. The medical event index is discussed in more detail hereinafter with respect to FIG. 4 and FIGS. 5A-5C.

FIG. 3 is intended to represent the major operations of an example method for generating a medical event index according to embodiments of the present disclosure. In some embodiments, however, individual operations can have greater or lesser complexity than shown in FIG. 3, and operations other than, or in addition to, those shown in FIG. 3 can be present. Furthermore, in some embodiments, various operations illustrated in FIG. 3 can have greater, lesser, or different functionality than shown in FIG. 3.

Figure 4:
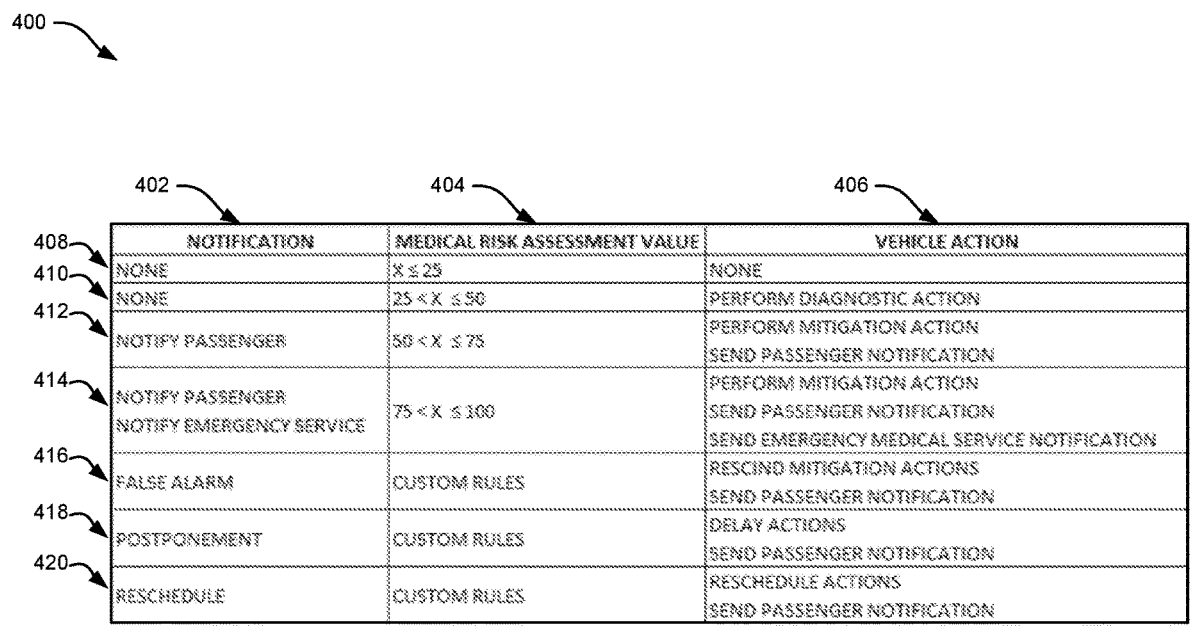
FIG. 4 illustrates an example medical index in accordance with some embodiments of the present disclosure.

FIG. 4 illustrates an example medical event index in accordance with some embodiments of the present disclosure. In some embodiments, the medical event index 400 is generated by a vehicular medical assistant (e.g., vehicular medical assistant 102 of FIG. 1 or vehicular medical assistant 1000 of FIG. 10). In other embodiments, the medical event index 400 is generated by an outside service and provided to the vehicular medical assistant via a physical or wireless network (e.g., network 150 of FIG. 1). In some embodiments, the medical event index 400 is consistent with the medical event index generated in operation 308 of FIG. 3 and/or medical event index 128 of FIG. 1.

Medical event index 400 can include relationships between notifications 402, medical risk assessment values 404, and vehicle actions 406. Medical risk assessment values 404 can be based on diagnostic data collected by the vehicular medical assistant (e.g., data collected from aural sensors, biometric sensors, visual sensors, and/or environmental sensors). In some embodiments, the medical risk assessment values 404 range from 0 (no medical event) to 100 (severe medical event). However, alternative ranges and/or scales can be used in alternative embodiments. Medical risk assessment values 404 are discussed in more detail hereinafter with respect to FIG. 5A.

Notifications 402 can include notifications to a passenger, an emergency contact, and/or an emergency authority (e.g., hospitals, urgent care centers, law enforcement, etc.). Notifications can be issued visually, verbally, and/or textually on an interface in a vehicle, to a dispatch center associated with an emergency authority, to a mobile phone associated with the passenger (or to a mobile phone of an emergency contact associated with the passenger), and/or to a wearable device associated with the passenger.

Vehicle actions 406 can include additional diagnostic actions, mitigation actions, and/or notification actions. Diagnostic actions can include collecting additional data (e.g., verifying an abnormal health condition), collecting additional types of data (e.g., requesting a diabetic passenger undergo a blood sugar test in response to detecting the passenger may be experiencing abnormal blood sugar levels), interacting with the passenger (e.g., asking the passenger a health-related question), or other diagnostic actions.

Mitigation actions can include rerouting the vehicle, altering the environmental conditions of the vehicle cabin, contacting an emergency authority, dispensing a medical aid to the passenger, notifying bystanders of the medical event, or other mitigation actions.

The medical event index 400 can include a variety of rules interrelating medical risk assessment values 404 with vehicle actions 406 and notifications 402. In a first example rule 408, there is no notification and no action associated with a score less than or equal to 25. In a second example rule 410, there is no notification but additional diagnostic testing with a score greater than 25 and less than or equal to 50. In a third example rule 412, the passenger is notified, and the vehicle performs a mitigation action for scores greater than 50 and less than or equal to 75. In a fourth example 414, the passenger is notified, an emergency service is notified, and a mitigation action is performed for scores greater than 75 and less than or equal to 100. In a fifth example 416, a false alarm is identified according to custom rules, the passenger is notified, and any mitigation actions are rescinded. In a sixth example 418, a diagnostic action and/or a mitigation action is postponed according to custom rules, and the passenger is notified. In a seventh example 420, a diagnostic action and/or a mitigation action is rescheduled according to custom rules, and the passenger is notified.

As will be appreciated by one skilled in the art, the example medical event index 400 illustrated in FIG. 4 can have alternative rules, ranges, scores, notifications, and actions while remaining within the spirit and scope of the present disclosure. Furthermore, some embodiments (e.g., embodiments based on neural networks) can comprise no table at all but rather a model that ingests data from sensors and outputs a score, a notification, a diagnostic action, and/or a mitigation action while remaining within the spirit and scope of the present disclosure.

FIGS. 5A-5C illustrate example data tables configured to collect data, score data, identify medical conditions, and select mitigation actions. In some embodiments, FIGS. 5A-5C are associated with medical event index 400 of FIG. 4. In some embodiments, FIGS. 5A-5C perform aspects of operation 202 of FIG. 2 and/or perform aspects of the method 300 of FIG. 3. The tables illustrated in FIGS. 5A-5C can be generated and maintained by a vehicular medical assistant (e.g., vehicular medical assistant 102 of FIG. 1 or 1000 of FIG. 10) or a different configuration of hardware and/or software.

FIG. 5A illustrates an example medical risk assessment value table 500. The medical risk assessment value table 500 can include sensors 502 associated with collected data 504, normal values 506, concerned values 508, emergency values 510, and scores 512. Sensors 502 can comprise sensors associated with a vehicular medical assistant (e.g., vehicular medical assistant 102 of FIG. 1 or 1000 of FIG. 10). In some embodiments, respective sensors 502 can be consistent with aural sensors 104, biometric sensors 106, visual sensors 108, and/or environmental sensors 110 of FIG. 1.

Data 504 can comprise data collected from sensors 502. The collected data can comprise numeric data (e.g., temperatures, blood pressures, heart rate, etc.), categorical data (e.g., normal or abnormal gesticulations), textual data (e.g., voice to text processing), and/or other data.

Normal values 506 can be typical values indicating stable health. Concerned values 508 can indicate ranges of values from sensors 502 associated with possible medical events. Concerned values 508 may not qualify as a medical event in isolation, but taken together with other values may indicate an emergent medical event. Emergency values 510 can comprise a range of values associated with respective sensors 502 that can indicate a medical event.

Scores 512 can comprise arithmetic and/or algebraic functions using data 504 as input. As shown, respective scores 512 for respective sensors 502 can include at least a weight value (e.g., W1 through WN) and a function (e.g., F1 through FN) utilizing a measured value (e.g., X1 through XN) from data 504.

Although individual scores 512 are shown, scores 512 can also be combined to generate an overall score. Individual scores 512 associated with respective sensors 502 (e.g., sub-scores) can be combined with other individual scores arithmetically (e.g., summed, etc.), algebraically (e.g., weighted, normalized, etc.), or using a different method. In some embodiments, scores 512 (or combinations of scores 512) can be used as medical risk assessment values 404 in the medical event index 400 of FIG. 4.

In some embodiments, normal values 506, concerned values 508, emergency values 510, and/or scores 512 can be defined based on cognitive learning performed on a corpus of medical data (e.g., operation 306 of FIG. 3).

For the purposes of illustration and as non-limiting examples, medical risk assessment value table 500 can include a first row 514 collecting a reading of 98 from a directional thermometer (e.g., biometric sensor) associated with a normal range 506, a concerned range 508, and an emergency range 510 which can be used to generate a score 512. As another example, a second row 516 can collect a reading of 18 corresponding to a number of blinks per minute collected from a camera (e.g., visual sensor) and associated with a normal range 506, a concerned range 508, an emergency range 510 which can together be used to generate a score 512. As another example, a third row 518 can classify passenger gesticulations collected from a camera (e.g., visual sensor) and associated with a set of normal gesticulations 506, a set of concerned gesticulations 508 (e.g., tremors), a set of emergency gesticulations 510 (e.g., hands on throat) which can together be used to generate a score 512. As another example, a fourth row 520 can collect verbal data using a microphone (e.g., aural sensor) and associated with a normal vocabulary 506, a concerned vocabulary 508 (e.g., the phrase "I'm not feeling well"), an emergency vocabulary (e.g., the phrase "help me") which can together be used to generate a score 512.

FIG. 5B illustrates an example medical condition table 522. Medical condition table 522 can include any number of medical conditions 524 such as, but not limited to, unconscious, fever, nauseous, choking, heart attack, and so on. Respective medical conditions 524 can be associated with respective sensor data rules 526. Sensor data rules 526 can be ranges (or combinations of ranges) of numeric data, types of categorical data (e.g., agitated gesticulation, abnormal heart rate, etc.), and/or specific phrases (e.g., a passenger saying "help", a retching sound, etc.).

In some embodiments, sensor data rules 526 can be compared with data 504 collected from sensors 502 to determine medical conditions 524. In some embodiments, medical conditions 524 comprise part of a notification 402 and/or part of a medical risk assessment value 404 as discussed in the medical event index 400 of FIG. 4.

FIG. 5C illustrates an example mitigation action table 528. Mitigation action table 528 can include any number of mitigation actions 530 executable by a vehicular medical assistant such as, but not limited to, attempting to wake a passenger using vehicle speakers, rerouting a vehicle, engaging emergency sirens and/or lights, requesting assistance using external speakers, notifying an emergency authority, increasing or decreasing the vehicle's cabin temperature, dispensing a medical aid, and so on. Respective mitigation actions 530 can be triggered by respective conditions 532. Respective conditions 532 can be based on medical conditions 524 and/or scores 512.

FIGS. 5A-5C are intended to represent the major components of example data tables configured for monitoring passenger health, scoring diagnostic data, identifying medical conditions, and/or selecting mitigation actions in accordance with embodiments of the present disclosure. In some embodiments, however, aspects of the data tables presented in FIGS. 5A-5C can have greater or lesser complexity than shown, and data tables other than, or in addition to, those shown in FIGS. 5A-5C can be present. Furthermore, in some embodiments, aspects of the data tables illustrated in FIGS. 5A-5C can have greater, lesser, or different functionality than shown in FIGS. 5A-5C.

Figure 6:
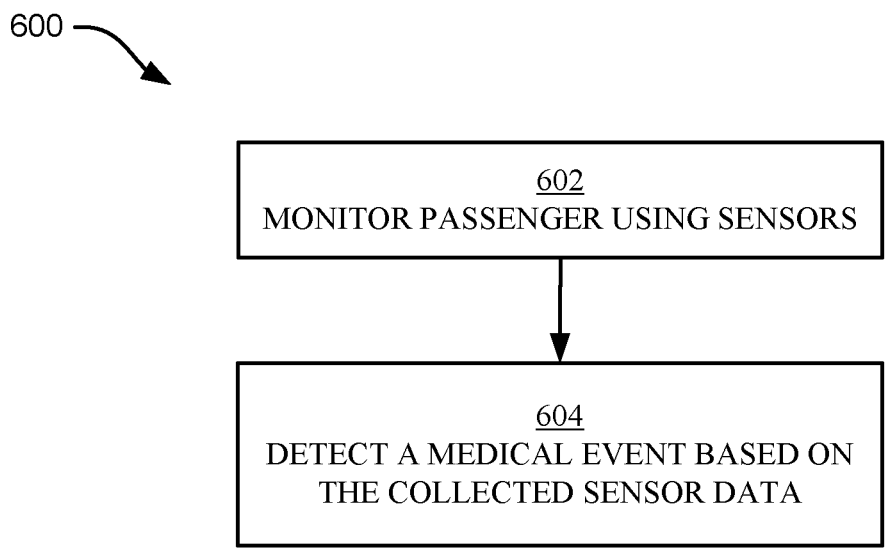
FIG. 6 illustrates a flowchart of an example method for detecting a medical event in accordance with some embodiments of the present disclosure.

FIG. 6 illustrates a flowchart of an example method for detecting a medical event in accordance with some embodiments of the present disclosure. In some embodiments, the method 600 is executed by a vehicular medical assistant (e.g., vehicular medical assistant 102 of FIG. 1 or vehicular medical assistant 1000 of FIG. 10), by a processor, or by a different set of hardware and software resources. For clarity, the method 600 will be described as being executed by a vehicular medical assistant, however, the method 600 can likewise be performed by alternative configurations of hardware. In some embodiments, the method 600 is a sub-method of operation 204 of FIG. 2.

In operation 602, the vehicular medical assistant can monitor a passenger using a set of sensors. The sensors can include, but are not limited to, aural sensors (e.g., aural sensors 104 of FIG. 1), biometric sensors (e.g., biometric sensors 106 of FIG. 1), visual sensors (e.g., visual sensors 108 of FIG. 1), and/or environmental sensors (e.g., environmental sensors 110 of FIG. 1). Data collected can be, but is not limited to, aural data (e.g., speech speed, speech volume, speech tone), biometric data (e.g., heart rate, body temperature, blood pressure, blood sugar level, etc.), visual data (e.g., gesticulations, coloration, perspiration, etc.), and/or environmental data (e.g., cabin temperature, humidity, etc.). In some embodiments, the data collected in operation 602 can be stored in a medical risk assessment value table (e.g., table 500 of FIG. 5A).

In operation 604, the vehicular medical assistant can detect a medical event based on the collected sensor data. In some embodiments, operation 604 further comprises determining a type of medical event based on the collected sensor data. In some embodiments, operation 604 further comprises determining an urgency of the medical event based on the collected sensor data. Operation 604 is described in more detail hereinafter with respect to FIG. 7.

In some embodiments, the medical event comprises a score above a threshold value, where the score is based on the collected sensor data (e.g., scores 512 of FIG. 5A). In some embodiments, the medical event comprises an identified medical condition, where the medical condition is identified based on the collected sensor data (e.g., medical conditions 524 of FIG. 5B).

FIG. 6 is intended to represent the major operations of an example method for identifying a medical event according to embodiments of the present disclosure. In some embodiments, however, individual operations can have greater or lesser complexity than shown in FIG. 6, and operations other than, or in addition to, those shown in FIG. 6 can be present. Furthermore, in some embodiments, various operations illustrated in FIG. 6 can have greater, lesser, or different functionality than shown in FIG. 6.

Figure 7:
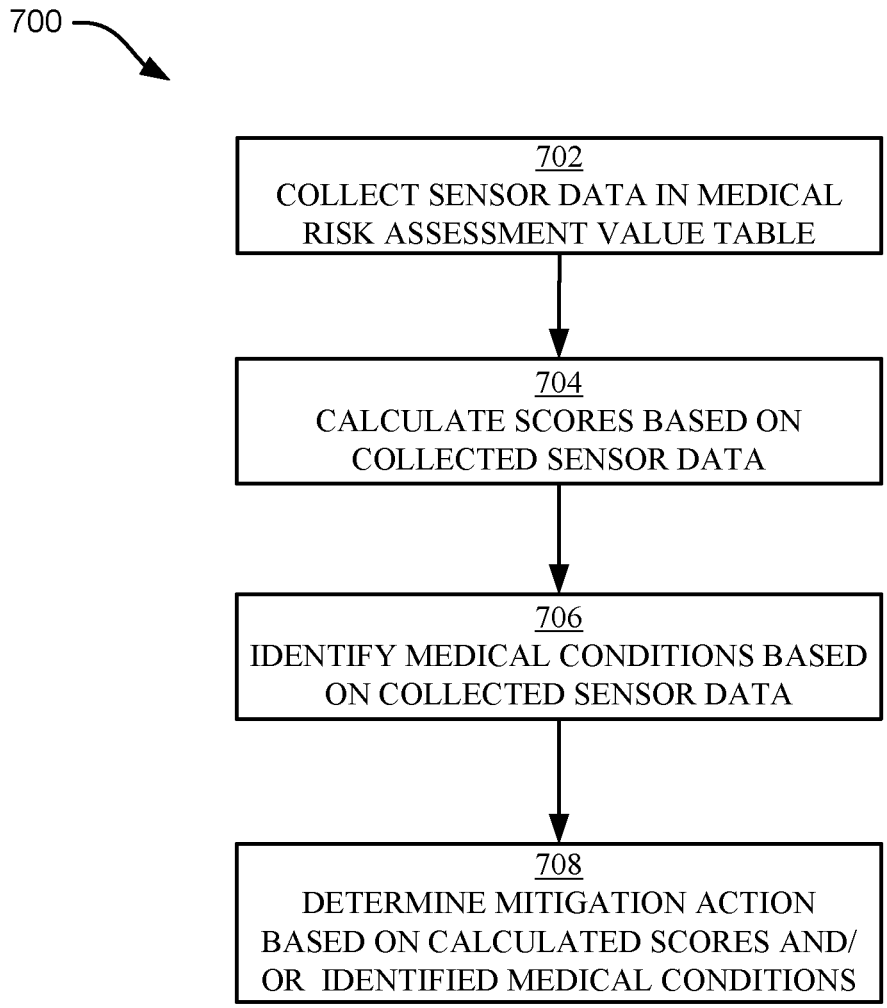
FIG. 7 illustrates a flowchart of an example method for detecting a medical event based on data tables in accordance with some embodiments of the present disclosure.

FIG. 7 illustrates a flowchart of an example method for detecting a medical event using data tables in accordance with some embodiments of the present disclosure. In some embodiments, the method 700 is executed by a vehicular medical assistant (e.g., vehicular medical assistant 102 of FIG. 1 or vehicular medical assistant 1000 of FIG. 10), by a processor, or by a different set of hardware and software resources. For clarity, the method 700 will be described as being executed by a vehicular medical assistant, however, the method 700 can likewise be performed by alternative configurations of hardware. In some embodiments, the method 700 is a sub-method of operation 204 of FIG. 2. In some embodiments, the method 700 is a sub-method of operation 604 of FIG. 6.

In operation 702, the vehicular medical assistant can collect sensor data in a medical risk assessment value table (e.g., the medical risk assessment value table 500 of FIG. 5A). In some embodiments, operation 702 comprises storing sensor data in the medical risk assessment value table at each predetermined increment of time (e.g., each 1 second, 5 seconds, 10 seconds, 30 seconds, etc.).

In operation 704, the vehicular medical assistant can calculate a medical risk assessment value based on the data collected in the medical risk assessment value table in operation 702 (e.g., based on aural data, biometric data, visual data, and/or environmental data). The medical risk assessment value score can comprise one or more sub-scores calculated for respective sensors. Respective sub-scores can be associated with respective weights and/or respective functions.

In operation 706, the vehicular medical assistant can identify a medical condition based on the collected sensor data. In some embodiments, operation 706 comprises identifying a medical condition using a medical condition table (e.g., medical condition table 522 of FIG. 5B). The medical condition table can identify respective medical conditions based on one or more scores calculated in operation 704.

In operation 708, the vehicular medical assistant can determine mitigation actions based on the score(s) calculated in operation 704 and/or based on the medical condition(s) identified in operation 706. In some embodiments, operation 708 includes identifying mitigation actions using a mitigation action table (e.g., mitigation action table 528 of FIG. 5C). In some embodiments, operation 708 further comprises implementing a mitigation action and notifying the user (e.g., verbally and/or visually) of the medical condition and the mitigation action.

FIG. 7 is intended to represent the major operations of an example method for detecting a medical event using data tables according to embodiments of the present disclosure. In some embodiments, however, individual operations can have greater or lesser complexity than shown in FIG. 7, and operations other than, or in addition to, those shown in FIG. 7 can be present. Furthermore, in some embodiments, various operations illustrated in FIG. 7 can have greater, lesser, or different functionality than shown in FIG. 7.

Figure 8:
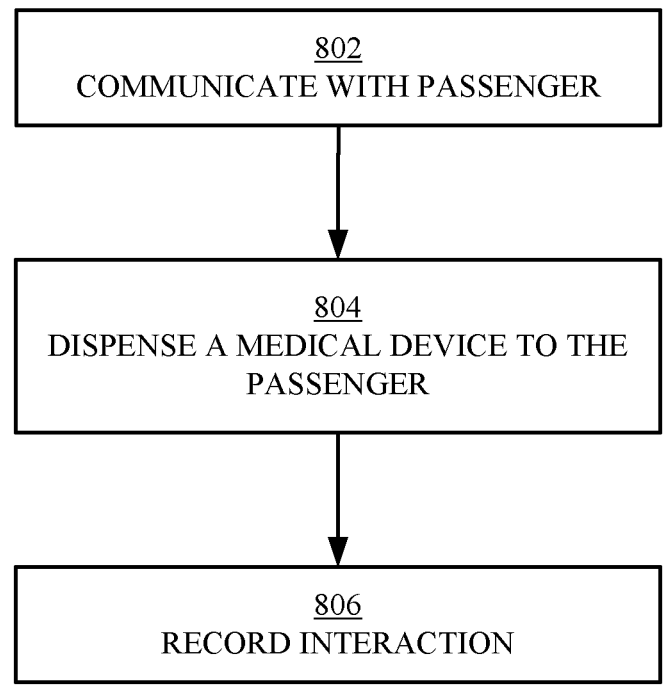
FIG. 8 illustrates a flowchart of an example method for interacting with a passenger in accordance with some embodiments of the present disclosure.

FIG. 8 illustrates a flowchart of an example method for interacting with a passenger during a medical event in accordance with some embodiments of the present disclosure. In some embodiments, the method 800 is executed by a vehicular medical assistant (e.g., vehicular medical assistant 102 of FIG. 1 or vehicular medical assistant 1000 of FIG. 10), by a processor, or by a different set of hardware and software resources. For clarity, the method 800 will be described as being executed by a vehicular medical assistant, however, the method 800 can likewise be performed by alternative configurations of hardware. In some embodiments, the method 800 is a sub-method of operation 206 of FIG. 2.

In operation 802, the vehicular medical assistant can communicate with the passenger. The vehicular medical assistant can communicate with the passenger verbally, textually, and/or visually in order to ask a question (e.g., gather additional health-related data), present instructions (e.g., indicate how to ameliorate a medical event), and/or provide a notification (e.g., indicate that an emergency authority was contacted and the vehicle was rerouted). For example, the vehicular medical assistant can communicate with the passenger using automated voice software to verbally ask the passenger a question. As another example, the vehicular medical assistant can present a textual question on a display device. As another example, the vehicular medical assistant can communicate with a passenger by presenting diagrammatic, pictographic, videographic, or other visual communications on a display device.

The vehicular medical assistant can receive feedback from the passenger verbally, tactilely, or otherwise. For example, the passenger can verbally respond to a question and the vehicular medical assistant can use voice-to-text software or other software to convert the verbal feedback to ingestible information. As another example, the passenger can interact with the vehicular medical assistant by providing tactile feedback such as, but not limited to, typing an answer, pushing a button on a touch screen, or performing a medical diagnostic test (e.g., by placing the passenger's arm in a blood pressure cuff).

In operation 804, the vehicular medical assistant can dispense a medical device to the passenger. Medical devices can include, but are not limited to, a bandage, an antiseptic, a disinfectant, a vomit bag, a medication, an epinephrine autoinjector, an opiate antidote, an inhaler, and/or a different medical device.

In operation 806, the vehicular medical assistant can record the interaction. For example, the vehicular medical assistant can notate the time, type, and reasoning (e.g., calculated scores, detected medical conditions, raw sensor data, etc.) for a dispensed medical aid together with a video showing the passenger consuming, applying, or otherwise using the dispensed medical aid. In some embodiments, operation 806 can further comprise sending the recording of the interaction, information regarding the passenger, information regarding the medical event, and/or information regarding the medical aid to an emergency authority.

In some embodiments, the recorded interaction is automatically encrypted. The recorded interaction can be automatically encrypted using a public-key encryption scheme (e.g., Diffie-Hellman encryption, Rivest-Shamir-Adleman (RSA) encryption, etc.), a symmetric-key encryption scheme (e.g., Data Encryption Standard (DES), triple-DES, Advanced Encryption Standard (AES), Rivest Cipher 4 (RC4, ARC4, or ARCFOUR), hash functions (e.g., MD4, MD5, SHA-1, SHA-2, etc.)), Schnorr signature encryption, El-Gamal encryption, Pretty good Privacy (PGP) encryption, interactive proof encryption, and/or other encryption schemes.

In some embodiments, the recorded interaction includes updating an immutable, distributed ledger (e.g., a blockchain) associated with the passenger medical history and/or a dispensed medical aid. For example, in some embodiments, a date, time, location, passenger identification, and passenger diagnostic data can be stored in an immutable, distributed ledge associated with the dispensed medical aid. In some embodiments, a date, time, location, passenger diagnostic data, and any vehicular actions or interactions can be recorded in an immutable, distributed ledger associated with the passenger identification and accessible to healthcare practitioners (e.g., an electronic health record).

FIG. 8 is intended to represent the major operations of an example method for interacting with a passenger during a medical event according to embodiments of the present disclosure. In some embodiments, however, individual operations can have greater or lesser complexity than shown in FIG. 8, and operations other than, or in addition to, those shown in FIG. 8 can be present. Furthermore, in some embodiments, various operations illustrated in FIG. 8 can have greater, lesser, or different functionality than shown in FIG. 8.

Figure 9:
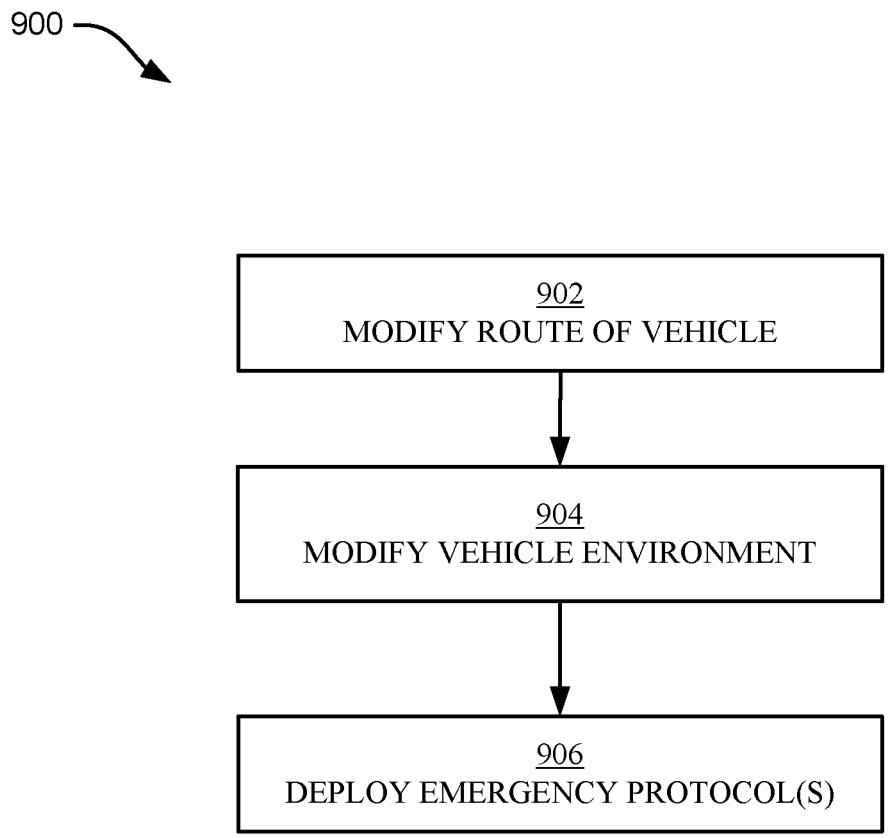
FIG. 9 illustrates a flowchart of an example method for modifying a vehicle in response to detecting a medical event in accordance with some embodiments of the present disclosure.

FIG. 9 illustrates a flowchart of an example method for modifying a vehicle during a medical event in accordance with some embodiments of the present disclosure. In some embodiments, the method 900 is executed by a vehicular medical assistant (e.g., vehicular medical assistant 102 of FIG. 1 or vehicular medical assistant 1000 of FIG. 10), by a processor, or by a different set of hardware and software resources. For clarity, the method 900 will be described as being executed by a vehicular medical assistant, however, the method 900 can likewise be performed by alternative configurations of hardware. In some embodiments, the method 900 is a sub-method of operation 208 of FIG. 2.

In operation 902, the vehicular medical assistant can modify a route of the vehicle. For example, in a non-autonomous vehicle, a new vehicle route can be presented on navigation equipment in the non-autonomous vehicle for the driver to follow. In a semi-autonomous vehicle, the vehicle can be autonomously rerouted to the side of the road and stopped. In an autonomous vehicle, the vehicle can be rerouted directly to a hospital, a clinic, a police station, a fire station, a rendezvous point, or a different location using autonomous driving features of the vehicle. In some embodiments, the vehicular medical assistant can calculate an estimated time of arrival based on the new route.

In some embodiments, the vehicular medical assistant can interact with a traffic service (e.g., traffic service 132 of FIG. 1) to choose between multiple locations based on estimated traffic condition (e.g., a first hospital may be geographically closer than a second hospital, but when accounting for traffic, the second hospital may be associated with an earlier arrival time than the first hospital). In such embodiments, the traffic service can be used to estimate an updated time of arrival accounting for traffic. In some embodiments, the traffic service deploys traffic shaping actions (e.g., traffic light manipulation, presenting notifications on electronic roadway signs, etc.) to reduce traffic delays associated with the route.

In some embodiments, the vehicular medical assistant can interact with a mobile emergency unit (e.g., mobile emergency unit 134) in order to create a rendezvous point between the vehicle and the mobile emergency unit.

In some embodiments, operation 902 further comprises notifying a destination (e.g., a hospital, a clinic, an emergency center, etc.) associated with the new route by providing an estimated time of arrival and/or information associated with the medical event.

In operation 904, the vehicular medical assistant can modify the vehicle environment. For example, the vehicular medical assistant can alter a cabin temperature of the vehicle by modifying a temperature control and/or a fan speed control of the heating and cooling system of the vehicle. As another example, the vehicular medical assistant can increase the noise level in the cabin of the vehicle in order to attempt to wake an unconscious or semi-conscious passenger.

In operation 906, the vehicular medical assistant can deploy one or more emergency protocols. Emergency protocols can include, but are not limited to, contacting an emergency authority (e.g., emergency service 130 of FIG. 1), turning on external hazard indicators, and/or requesting bystander help. An emergency authority can be contacted by broadcasting, calling, emailing, transmitting an emergency code, or otherwise notifying the emergency authority. External hazard indicators can include, but are not limited to, lights, sirens, and speakers. Requesting bystander help can include indicating the nature of the medical event using an external speaker and/or broadcasting the nature of the medical event to surrounding vehicles via a wireless broadcasting technique.

Wireless broadcasting techniques can include, but are not limited to, ANT/ANT+, Bluetooth, cellular (e.g., 3G, 4G, 5G, etc.), infrared, the Industrial, Scientific, and Medical (ISM) band, 6LoWPAN, ultra-wideband (UWB), Wi Fi, wirelessHART, WirelessHD, techniques conforming to Institute of Electrical and Electronics Engineers (IEEE) standards such as IEEE 802.15.4 and IEEE 802.22, techniques conforming to International Standards of Automation (ISA) standards such as ISA100a, and/or different techniques.

FIG. 9 is intended to represent the major operations of an example method for modifying a vehicle during a medical event according to embodiments of the present disclosure. In some embodiments, however, individual operations can have greater or lesser complexity than shown in FIG. 9, and operations other than, or in addition to, those shown in FIG. 9 can be present. Furthermore, in some embodiments, various operations illustrated in FIG. 9 can have greater, lesser, or different functionality than shown in FIG. 9.

Figure 10:
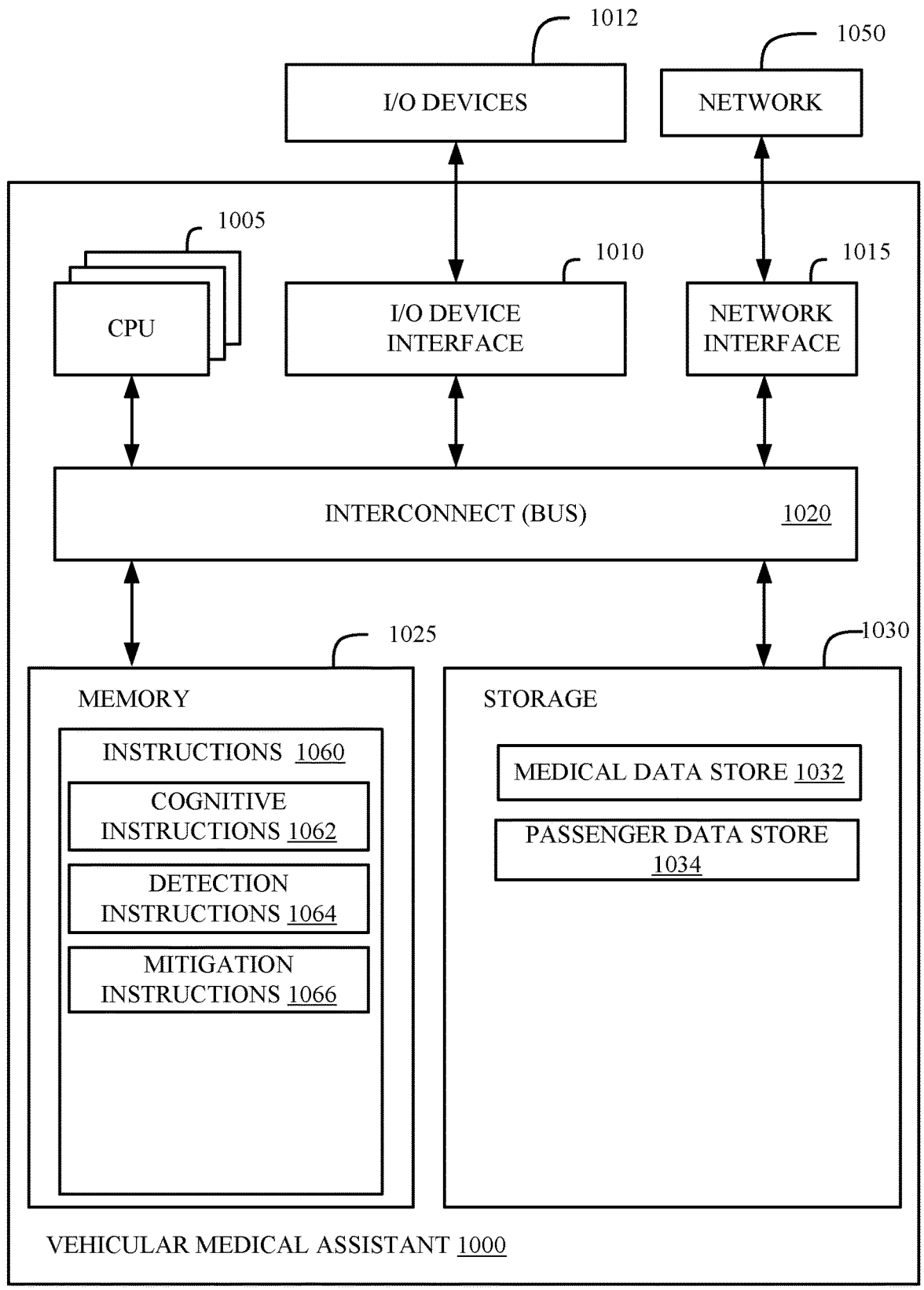
FIG. 10 illustrates a block diagram of an example vehicular medical assistant in accordance with some embodiments of the present disclosure.

FIG. 10 illustrates a block diagram of a vehicular medical assistant 1000 in accordance with some embodiments of the present disclosure. In some embodiments, vehicular medical assistant 1000 is consistent with vehicular medical assistant 102 of FIG. 1. In various embodiments, vehicular medical assistant 1000 performs any of the methods described in FIGS. 2-3 and/or 6-9. In some embodiments, vehicular medical assistant 1000 provides instructions for one or more of the methods described in FIGS. 2-3 and/or 6-9 to a client machine such that the client machine executes the method, or a portion of the method, based on the instructions provided by the vehicular medical assistant 1000. In some embodiments, vehicular medical assistant 1000 generates, maintains, and/or utilizes (or provides instructions to a client machine for the client machine to generate, maintain, and/or utilize) any of the tables presented in FIG. 4 and/or FIGS. 5A-5C.

The vehicular medical assistant 1000 includes a memory 1025, storage 1030, an interconnect (e.g., BUS) 1020, one or more CPUs 1005 (also referred to as processors 1005 herein), an I/O device interface 1010, I/O devices 1012, and a network interface 1015.

Each CPU 1005 retrieves and executes programming instructions stored in the memory 1025 or storage 1030. The interconnect 1020 is used to move data, such as programming instructions, between the CPUs 1005, I/O device interface 1010, storage 1030, network interface 1015, and memory 1025. The interconnect 1020 can be implemented using one or more busses. The CPUs 1005 can be a single CPU, multiple CPUs, or a single CPU having multiple processing cores in various embodiments. In some embodiments, a CPU 1005 can be a digital signal processor (DSP). In some embodiments, CPU 1005 includes one or more 3D integrated circuits (3DICs) (e.g., 3D wafer-level packaging (3DWLP), 3D interposer based integration, 3D stacked ICs (3D-SICs), monolithic 3D ICs, 3D heterogeneous integration, 3D system in package (3DSiP), and/or package on package (PoP) CPU configurations). Memory 1025 is generally included to be representative of a random access memory (e.g., static random access memory (SRAM), dynamic random access memory (DRAM), or Flash). The storage 1030 is generally included to be representative of a non-volatile memory, such as a hard disk drive, solid state device (SSD), removable memory cards, optical storage, or flash memory devices. In an alternative embodiment, the storage 1030 can be replaced by storage area-network (SAN) devices, the cloud, or other devices connected to the vehicular medical assistant 1000 via the I/O devices interface 1010 or a network 1050 via the network interface 1015.

In some embodiments, the memory 1025 stores instructions 1060 and the storage 1030 stores medical data store 1032 and passenger data store 1034. However, in various embodiments, the instructions 1060, the medical data store 1032, and the passenger data store 1034 are stored partially in memory 1025 and partially in storage 1030, or they are stored entirely in memory 1025 or entirely in storage 1030, or they are accessed over a network 1050 via the network interface 1015.

Medical data store 1032 can be consistent with medical data store 120 of FIG. 1. Medical data store 1032 can include information useful for monitoring health, diagnosing medical events, and/or mitigating medical events. Medical data store 1032 can include normal, abnormal, and emergent ranges of various diagnostic measurements.

Passenger data store 1034 can be consistent with passenger data 138 of FIG. 1. Passenger data store 1034 can store historical health data for a passenger. Passenger data store 1034 can retrieve data from, for example, wearable devices, applications stored on a mobile phone, or other devices.

The instructions 1060 are processor executable instructions including cognitive instructions 1062, detection instructions 1064, and mitigation instructions 1066.

Cognitive instructions 1062 can comprise processor-executable instructions configured to generate models, ranges, scores, correlations, indications, predictions, expectations, confidence levels, thresholds, and/or other interrelationships useful for detecting and mitigating medical events. In some embodiments, cognitive instructions 1062 can perform operation 202 of FIG. 2 and/or the method 300 of FIG. 3. In some embodiments, cognitive instructions 1062 can generate medical event index 400 of FIG. 4, medical risk assessment value table 500 of FIG. 5A, medical condition table 522 of FIG. 5B, and/or mitigation action table 528 of FIG. 5C.

Detection instructions 1064 can comprise processor-executable instructions configured to detect medical events. In some embodiments, detection instructions 1064 can perform operation 204 of FIG. 2, the method 600 of FIG. 6 and/or the method 700 of FIG. 7. In some embodiments, detection instructions 1064 can maintain (e.g., populate and utilize) medical event index 400 of FIG. 4, medical risk assessment value table 500 of FIG. 5A, medical condition table 522 of FIG. 5B, and/or mitigation action table 528 of FIG. 5C.

Mitigation instructions 1064 can comprise processor-executable instructions configured to mitigate medical events. In some embodiments, mitigation instructions 1064 can perform operations 206 and/or 208 of FIG. 2, the method 800 of FIG. 8, and/or the method 900 of FIG. 9.

In various embodiments, the I/O devices 1012 include an interface capable of presenting information and receiving input (e.g., user interface 118 of FIG. 1). For example, I/O devices 1012 can present information to a user (e.g., a question, instructions regarding a detected medical event, a notification of a mitigation action, etc.) interacting with vehicular medical assistant 1000 and receive input from a user (e.g., an answer to a question, a confirmation, etc.).

Vehicular medical assistant 1000 is connected to the network 1050 via the network interface 1015. In some embodiments, network 1050 is consistent with network 150 of FIG. 1.

FIG. 10 is intended to represent the major components of an example vehicular medical assistant 1000 according to embodiments of the present disclosure. In some embodiments, however, individual components can have greater or lesser complexity than shown in FIG. 10, and components other than, or in addition to those shown in FIG. 10 can be present. Furthermore, in some embodiments, various components illustrated in FIG. 10 can have greater, lesser, or different functionality than shown in FIG. 10.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 11:
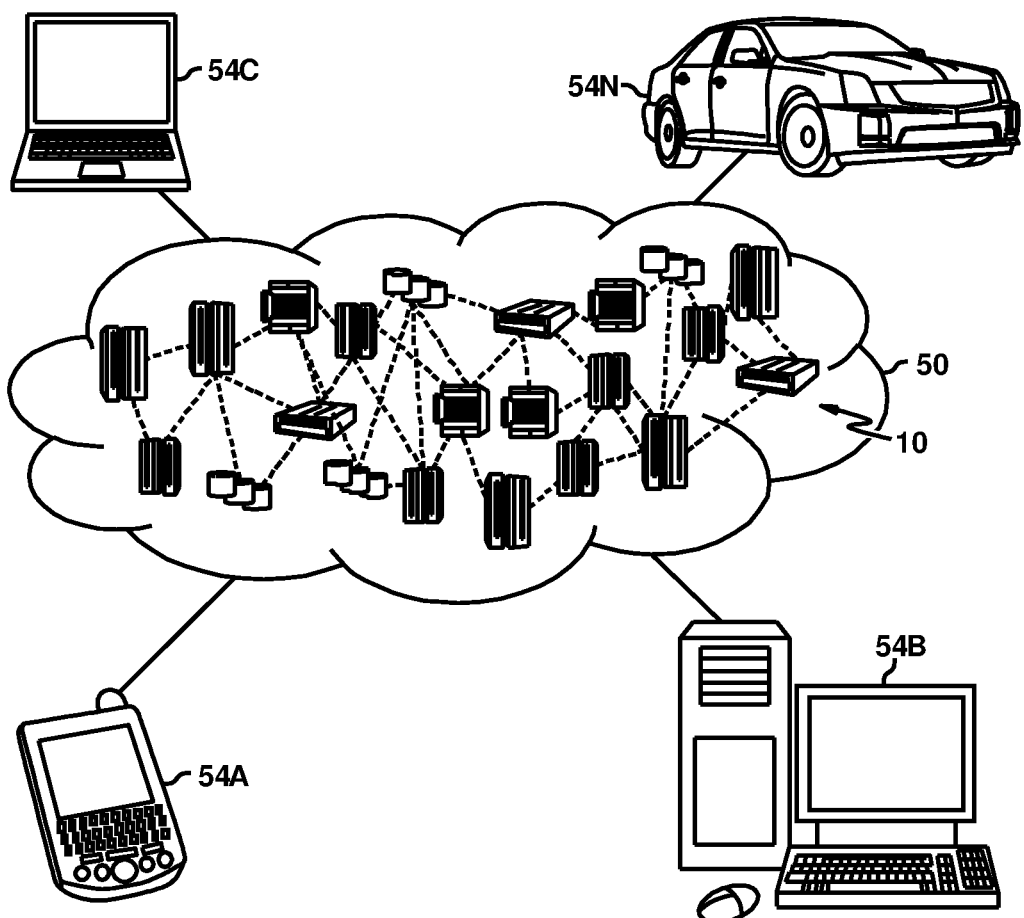
FIG. 11 depicts a cloud computing environment according to some embodiments of the present disclosure.

Referring now to FIG. 11, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 11 are intended to be illustrative only and that computing nodes 10 and cloud computing environment 50 can communicate with any type of computerized device over any type of network and/or network addressable connection (e.g., using a web browser).

Figure 12:
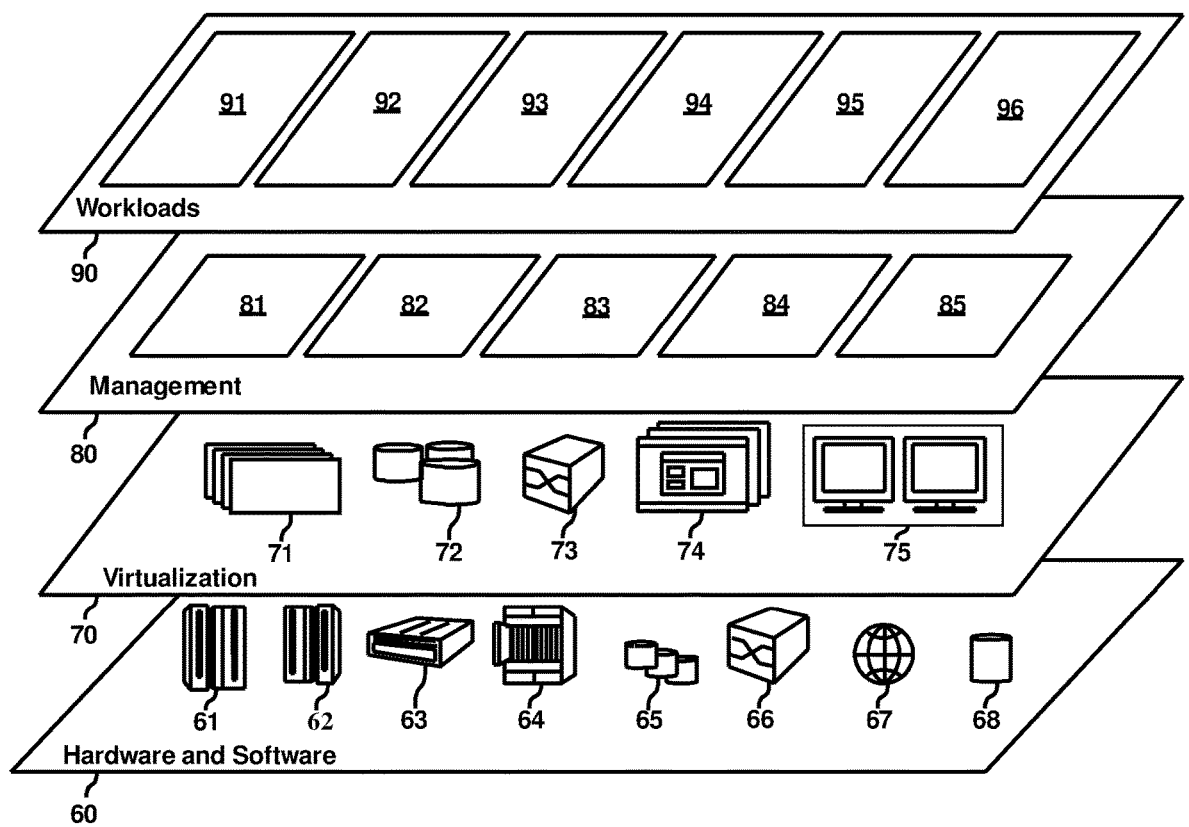
FIG. 12 depicts abstraction model layers according to some embodiments of the present disclosure.

Referring now to FIG. 12, a set of functional abstraction layers provided by cloud computing environment 50 (FIG. 11) is shown. It should be understood in advance that the components, layers, and functions shown in FIG. 12 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and vehicular medical assistance 96.

Embodiments of the present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or subset of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While it is understood that the process software (e.g., any of the instructions stored in instructions 1060 of FIG. 10 and/or any software configured to perform any subset of the methods described with respect to FIGS. 2-3 and 6-9) may be deployed by manually loading it directly in the client, server, and proxy computers via loading a storage medium such as a CD, DVD, etc., the process software may also be automatically or semi-automatically deployed into a computer system by sending the process software to a central server or a group of central servers. The process software is then downloaded into the client computers that will execute the process software. Alternatively, the process software is sent directly to the client system via e-mail. The process software is then either detached to a directory or loaded into a directory by executing a set of program instructions that detaches the process software into a directory. Another alternative is to send the process software directly to a directory on the client computer hard drive. When there are proxy servers, the process will select the proxy server code, determine on which computers to place the proxy servers' code, transmit the proxy server code, and then install the proxy server code on the proxy computer. The process software will be transmitted to the proxy server, and then it will be stored on the proxy server.

Embodiments of the present invention may also be delivered as part of a service engagement with a client corporation, nonprofit organization, government entity, internal organizational structure, or the like. These embodiments may include configuring a computer system to perform, and deploying software, hardware, and web services that implement, some or all of the methods described herein. These embodiments may also include analyzing the client's operations, creating recommendations responsive to the analysis, building systems that implement subsets of the recommendations, integrating the systems into existing processes and infrastructure, metering use of the systems, allocating expenses to users of the systems, and billing, invoicing, or otherwise receiving payment for use of the systems.

What is claimed is:

1. A computer-implemented method for mitigating a medical event in a vehicle, the method comprising:
    downloading instructions to the vehicle from a server data processing system to provide vehicular medical assistant functionality to the vehicle;
    accessing a medical data store comprising diagnostic data, medical conditions, and mitigation actions, wherein the diagnostic data, medical conditions, and mitigation actions are interrelated using machine learning algorithms;
    detecting a medical event based on a set of data associated with a passenger in the vehicle and the medical data store, wherein the set of data associated with the passenger is received from a plurality of sensors in the vehicle, wherein the plurality of sensors comprises a biometric sensor collecting biometric data from the passenger, an aural sensor collecting aural data from the passenger, a visual sensor collecting visual data from the passenger, and an environmental sensor collecting environmental data from the vehicle, wherein the set of data associated with the passenger comprises the aural data, the biometric data, the visual data, and the environmental data;
    implementing a mitigation action in response to detecting the medical event, wherein the mitigation action comprises an interaction with the passenger and a modification to the vehicle;
    metering use of the vehicular medical assistant functionality in the vehicle; and
    generating an invoice in response to metering use of the vehicular medical assistant functionality.

2. The method according to claim 1, wherein accessing the medical data store further comprises:
    retrieving a corpus of medical data, wherein the corpus of medical data comprises diagnostic data, medical condition data, and mitigation data;
    performing cognitive learning on the corpus of medical data; and
    generating a medical event index based on performing cognitive learning on the corpus of medical data, wherein the medical event index interrelates medical risk assessment values, notifications, and mitigation actions.

3. The method according to claim 2, wherein detecting a medical event further comprises:
    calculating a first medical risk assessment value based on the aural data, the biometric data, the visual data, and the environmental data; and
    identifying a medical condition based on the aural data, the biometric data, the visual data, and the environmental data.

4. The method according to claim 3, wherein implementing a mitigation action further comprises:
    identifying a first mitigation action based on the first medical risk assessment value and the medical event index;
    implementing the first mitigation action; and
    notifying the passenger of the medical condition and the first mitigation action.

5. The method according to claim 1, wherein implementing a mitigation action further comprises:
    communicating with the passenger regarding the medical event; and
    dispensing a medical aid to the passenger.

6. The method according to claim 1, wherein implementing a mitigation action further comprises:
    modifying a route of the vehicle, using autonomous driving features, to an emergency center using a first route.

7. The method according to claim 6, wherein modifying a route of the vehicle to an emergency center further comprises:
    communicating with a traffic service to identify the first route and determine an estimated arrival time; and
    notifying the emergency center of the medical event, the first route, and the estimated arrival time.

8. The method according to claim 1, wherein implementing a mitigation action further comprises:
    altering a temperature of the vehicle by modifying a temperature control and a fan speed control of the vehicle.

9. The method according to claim 1, wherein implementing a mitigation action further comprises:
    notifying an emergency authority of the medical event and a location of the vehicle.

10. A system for mitigating a medical event in a vehicle, the system comprising:
    a processor; and
    a computer-readable storage medium storing instructions, which, when executed by the processor, are configured to cause the processor to perform a method, wherein the computer readable storage medium storing the instructions is located in a server data processing system, and wherein the instructions are downloaded over a network to the vehicle to provide vehicular medical assistant functionality to the vehicle, the method comprising:
        accessing a medical data store comprising diagnostic data, medical conditions, and mitigation actions, wherein the diagnostic data, medical conditions, and mitigation actions are interrelated using machine learning algorithms;
        detecting a medical event based on a set of data associated with a passenger in the vehicle and the medical data store, wherein the set of data associated with the passenger is received from a plurality of sensors in the vehicle, wherein the plurality of sensors comprises a biometric sensor collecting biometric data from the passenger, an aural sensor collecting aural data from the passenger, a visual sensor collecting visual data from the passenger, and an environmental sensor collecting environmental data from the vehicle, wherein the set of data associated with the passenger comprises the aural data, the biometric data, the visual data, and the environmental data;

implementing a mitigation action in response to detecting the medical event, wherein the mitigation action comprises an interaction with the passenger and a modification to the vehicle;

metering use of the vehicular medical assistant functionality in the vehicle; and generating an invoice in response to metering use of the vehicular medical assistant functionality.

11. The system according to claim 10, wherein accessing the medical data store further comprises:

retrieving a corpus of medical data, wherein the corpus of medical data comprises diagnostic data, medical condition data, and mitigation data;

performing cognitive learning on the corpus of medical data; and generating a medical event index based on performing cognitive learning on the corpus of medical data, wherein the medical event index interrelates medical risk assessment values, notifications, and mitigation actions.

12. The system according to claim 11, wherein implementing a mitigation action further comprises:

identifying a first mitigation action based on the aural data, the biometric data, the visual data, the environmental data, and the medical event index;

implementing the first mitigation action; and notifying the passenger of the first mitigation action.

13. The system according to claim 10, wherein implementing a mitigation action further comprises:

communicating with the passenger regarding the medical event;

dispensing a medical aid to the passenger;

storing a recording of the passenger using the medical aid; and sending the recording, first information regarding the medical event, and second information regarding the medical aid to an emergency authority.

14. The system according to claim 10, wherein implementing a mitigation action further comprises:

modifying a route of the vehicle, using autonomous driving features, to an emergency center using a first route.

15. The system according to claim 10, wherein implementing a mitigation action further comprises:

altering the vehicle by modifying an environmental control of the vehicle.

16. A computer program product for mitigating a medical event in a vehicle, the computer program product comprising a computer readable storage medium having program instructions embodied therewith, wherein the computer readable storage medium is not a transitory signal per se, wherein the computer readable storage medium storing the program instructions is located in a server data processing system, and wherein the instructions are downloaded over a network to the vehicle to provide vehicular medical assistant functionality to the vehicle, the program instructions executable by a processor to cause the processor to perform a method comprising:

accessing a medical data store comprising diagnostic data, medical conditions, and mitigation actions, wherein the diagnostic data, medical conditions, and mitigation actions are interrelated using machine learning algorithms;

detecting a medical event based on a set of data associated with a passenger in the vehicle and the medical data store, wherein the set of data associated with the passenger is received from a plurality of sensors in the vehicle, wherein the plurality of sensors comprises a biometric sensor collecting biometric data from the passenger, an aural sensor collecting aural data from the passenger, a visual sensor collecting visual data from the passenger, and an environmental sensor collecting environmental data from the vehicle, wherein the set of data associated with the passenger comprises the aural data, the biometric data, the visual data, and the environmental data;

implementing a mitigation action in response to detecting the medical event, wherein the mitigation action comprises an interaction with the passenger and a modification to the vehicle;

metering use of the vehicular medical assistant functionality in the vehicle; and generating an invoice in response to metering use of the vehicular medical assistant functionality.

17. The computer program product according to claim 16, wherein computer readable storage medium storing the program instructions is located in the vehicle, and wherein the program instructions were downloaded over a network from a remote data processing system.

18. The computer program product according to claim 16, wherein the biometric sensor comprises a directional thermometer and an odor sensor, wherein the aural sensor comprises a microphone, wherein the visual sensor comprises a camera, and wherein the environmental sensor comprises an accelerometer.

* * * * *